US005807251A

United States Patent [19]

Wang et al.

[11] Patent Number: 5,807,251

[45] Date of Patent: Sep. 15, 1998

[54] ELECTRICAL IMPEDANCE TOMOGRAPHY

[75] Inventors: Mi Wang, Manchester; Fraser John Dickin, Nr Crewe; Richard Andrew Williams, Falmouth, all of England

[73] Assignee: British Technology Group Limited, London, England

[21] Appl. No.: 700,370

[22] PCT Filed: Mar. 10, 1995

[86] PCT No.: PCT/GB95/00520

§ 371 Date: Aug. 26, 1996

§ 102(e) Date: Aug. 26, 1996

[87] PCT Pub. No.: WO95/24155

PCT Pub. Date: Sep. 14, 1995

[30] Foreign Application Priority Data

| | | | |
|---|---|---|---|
| Mar. 11, 1994 | [GB] | United Kingdom | 9404766 |
| Mar. 23, 1994 | [GB] | United Kingdom | 9405794 |
| Nov. 25, 1994 | [GB] | United Kingdom | 9424129 |

[51] Int. Cl.$^{6}$ .................... A61B 5/05

[52] U.S. Cl. .................... 600/407; 600/547

[58] Field of Search .................... 128/653.1, 734, 128/922, 640; 607/148, 149; 600/407, 506, 547; 324/600, 629

[56] References Cited

U.S. PATENT DOCUMENTS

| | | | |
|---|---|---|---|
| 4,709,704 | 12/1987 | Lukasiewicz | 128/644 |
| 4,974,598 | 12/1990 | John . | |
| 5,020,541 | 6/1991 | Marriott . | |
| 5,184,624 | 2/1993 | Brown et al. | 128/734 |
| 5,284,142 | 2/1994 | Goble et al. | 128/653.1 |
| 5,311,878 | 5/1994 | Brown et al. | 128/734 |
| 5,351,697 | 10/1994 | Cheney et al. . | |
| 5,353,802 | 10/1994 | Ollmar | 128/734 |
| 5,381,333 | 1/1995 | Isaacson et al. . | |
| 5,390,110 | 2/1995 | Cheney et al. . | |
| 5,421,345 | 6/1995 | Lekholm et al. | 128/734 |
| 5,465,730 | 11/1995 | Zadehkoochak et al. | 128/734 |
| 5,544,662 | 8/1996 | Saulnier et al. | 128/734 |
| 5,560,372 | 10/1996 | Cory . | |
| 5,575,292 | 11/1996 | Brown et al. . | |
| 5,626,146 | 5/1997 | Barber et al. | 128/734 |
| 5,657,552 | 8/1997 | Reineck et al. . | |

OTHER PUBLICATIONS

Ping Hua et al, "Using Compound Electrodes in Electrical Impedance Tomography", IEEE Transactions on Biomedical Engineering, vol. 40 No. 1, Jan. 1993.

F.J. Dickin et al "Determination of Composition and Motion of . . . ", Chemical Engineering Science, vol. 48 No. 10 pp. 1883–1897, 1993.

C J Kotre, "A Sensitivity coefficient method for the reconstruction of . . . ", Clin. Phys. Physiol Meas., 1989 vol. 10 No. 3, pp. 275–281.

*Primary Examiner*—William E. Kamm
*Assistant Examiner*—Shawna J. Shaw
*Attorney, Agent, or Firm*—Cushman Darby & Cushman IP Group of Pillsbury Madison & Sutro LLP

[57] ABSTRACT

Method and apparatus for obtaining a representation of the distribution of electrical impedance within material contained within a containing wall, comprising providing a plurality of mutually spaced electrodes mounted at spaced locations of the wall, electrically insulated from one another and arranged to be in electrical contact with material contained within the wall, applying between an electrical reference ground and each electrode, separately, an input electrical signal which, while applied to any one of the electrodes, causes respective output electrical signals to be generated between the reference ground and each other one of the electrodes, measuring the output electrical signals and processing the resulting measured data to provide a representation of the distribution, within the said material, of its electrical impedance.

17 Claims, 5 Drawing Sheets

ELECTRICAL IMPEDANCE TOMOGRAPHY

This application claims benefit of international application PCT/GB95/00520filed Mar. 10, 1995.

This invention relates to electrical impedance tomography (EIT), which has been known for some time in clinical applications and has recently gained acceptance as a useful technique for rapidly delineating the resistivity distribution of materials inside a process vessel or pipeline.

In the clinical use of EIT, it is known to provide a set of electrodes spaced around, say, the thorax of a patient in electrical contact with the skin, and to apply a constant current or constant voltage input electrical signal between each in turn of all the possible mutually adjacent pairs of electrodes. While the input signal is being applied to any one pair of mutually adjacent electrodes, the currents or voltages between each mutually adjacent pair of the remainder of the electrodes are measured and the resulting measured-data are processed in known manner to yield, and display on a screen, a representation of the distribution of the electrical resistivity across a cross section of the patient which is bounded by the ring of electrodes.

It is also known from U.S. Pat. 5,272,624 to employ a medical electrical impedance imaging technique using set current patterns, in which electrical current is simultaneously injected to each of an array of spaced electrodes around the periphery of the body under investigation, the amplitude of the current varying according to, say, a cosinusoidal distribution around the periphery. The pattern of injected current is then successively altered around the electrode array, and the amplitude of the input signal is adapted to give the optimum distinguishability for the particular application of interest.

The technique of U.S. Pat. No. 5,272,624 involves the measurement of the voltages developed at or near each electrode with respect to a common point, or earth reference. However, the currents are injected independently of this earth reference.

It has also become known to apply EIT to vessels and pipelines made of electrically non-conductive material, such as acrylic or other plastics materials, in order to determine the resistivity distribution, over a cross-section of the vessel or pipeline, of its contents, notably when these are or may be a suspension of solids in a liquid of different resistivity, or a plurality of mutually immiscible liquids of different resistivities. In this application of EIT, it is known to provide that the electrodes are mounted in and project through the vessel or pipeline wall so as to be directly in electrical contact with the contents within. Only a minor modification of the data processing algorithm is required to take account of the fact that the pairs of electrodes between which an input signal is applied or an output signal is measured may now be actually or effectively within (though usually only slightly within) the body of material of which the resistivity distribution is to be determined.

It has also been proposed to employ EIT in connection with vessels and pipelines made of electrically conductive materials. Clearly, since most industrial pipelines and process vessels are constructed from electrically conductive metallic materials, there is a practical need to modify existing EIT techniques as may be necessary to accommodate such materials. Since it is necessary to keep the electrodes insulated from one another, it is necessary to insulate them from the conductive containing wall and to arrange that they project through the wall into direct electrical contact with the contents within. Even when that is done, however, it is found that, when an input signal is applied between one pair of adjacent electrodes, output signals measured between other pairs of mutually adjacent electrodes are of low amplitude and consequently have a poor signal-to-noise ratio leading, after signal processing in known manner, to a resistivity-distribution determination of unsatisfactorily poor quality.

A useful summary of the applications of EIT to fluid mixtures in process reactors and pipelines can be found in "Determination of Composition and Motion of Multicomponent Mixtures in Process Vessels using Electrical Impedance Tomography-I. Principles and Process Engineering Applications" F. J. Dickin et al, Chemical Engineering Science, Vol. 48, No. 10, 1993, pp. 1883–1897.

SUMMARY OF THE INVENTION

It is an object of the present invention to provide an EIT method and apparatus which may be successfully employed in conjunction with a containing wall of either electrically non-conductive or electrically conductive material.

According to a first aspect of the invention there is provided a method of obtaining a representation of the distribution of electrical impedance within material contained within a containing wall, comprising providing a plurality of mutually spaced electrodes mounted at spaced locations of the wall, electrically insulated from one another and arranged to be in electrical contact with material contained within the wall, applying between an electrical reference ground and each electrode, separately, an input electrical signal which, while applied to any one of the electrodes, causes respective output electrical signals to be generated between the reference ground and each other one of the electrodes, measuring the output electrical signals and processing the resulting measured data to provide a representation of the distribution, within the said material, of its electrical impedance.

According to another aspect of the invention there is provided apparatus for obtaining a representation of the distribution of electrical impedance within a body of material, comprising container means having a containing wall for containing the material, a plurality of electrodes mounted at spaced locations of the wall, electrically insulated from one another and arranged to be in electrical contact with material contained within the wall, means for generating, and applying between an electrical reference ground and each electrode, separately, an input signal which, while applied to any one of the electrodes, causes respective output electrical signals to be generated between the reference ground and each other one of the electrodes, means for measuring the output electrical signals, and means for processing the resulting measured data and providing a representation of the distribution, within the said material, of its electrical impedance.

In applying the method and apparatus according to the invention in a case where the containing wall is of electrically conductive material, the wall itself is preferably made to serve as the reference ground relative to which the input and output electrical signals are applied and measured, preferably with the electrodes mounted in the wall but electrically insulated from it, and protruding through it into contact with the material contained within it.

If the containing wall is non-conductive, other means of providing the reference ground must be devised. To that end, it may be arranged that the reference ground is constituted, at any given moment, by all the electrodes, electrically strapped together, except for one of the electrodes to which an input signal is being applied relative to the reference ground, and one other of the electrodes at which an output electrical signal is being measured relative to the reference ground.

In another embodiment of the invention, the reference ground is provided by at least one electrode positioned within, and away from the boundary of, the material whose impedance distribution is to be reconstructed. This reference ground electrode may or may not be positioned at the centre of the vessel. If an electrically conductive component of the apparatus, such as a stirrer, is positioned within the vessel it may be made to serve as the reference ground electrode.

In a modification, in clinical use of the invention, the patient's skin constitutes the boundary of the material whose impedance distribution is to be reconstructed, and no other containing wall requires to be provided. In such a case, the electrodes are applied to the skin in known manner and are not required to protrude through it.

BREIF DESCRIPTION OF THE DRAWINGS

The invention will be further explained and elucidated in the following description referring to both method and apparatus, with reference to the accompanying drawings, in which.

DETAILED DESCRIPTION OF THE PRESENTLY PRREFERRED EXEMPLARY EMBODIMENT

Figure 1:
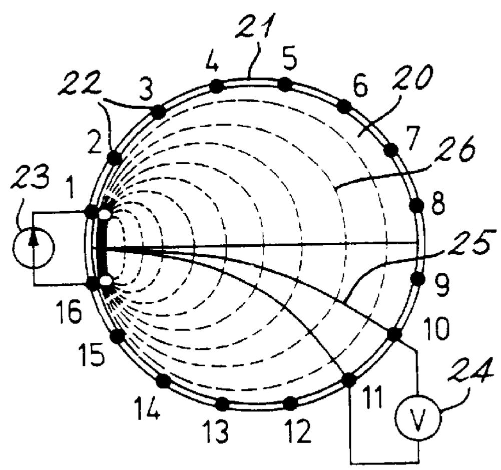
FIG. 1 represents a known kind of EIT applied to material contained in a circular-section vessel or pipeline of which the containing wall is of electrically non- conductive material.

In the known application of EIT illustrated in FIG. 1, material 20 of which the resistivity distribution is to be determined is contained in a pipeline or other vessel having a circular wall 21 of acrylic or other electrically insulating material, and a plurality of electrodes 22 are mounted in the wall 21, equally spaced around it and each projecting through the wall so as to be in contact, inside the wall, with the material 20 and accessible, outside the wall, for attachment of an electrical connection. As shown diagrammatically in FIG. 1, a source 23 of constant current is connected between one mutually adjacent pair of the electrodes 22, and a voltage measuring device 24 is connected between a mutually adjacent pair of the remaining electrodes 22 to measure the voltage existing between those electrodes in consequence of the current flowing between the pair of electrodes to which the source 23 is connected. In performing this form of EIT, the current source 23 would be maintained connected between the one pair of mutually adjacent electrodes while the voltages between each other mutually adjacent pair of the remaining electrodes is similarly measured. The current source 23 would then be connected between a different pair of mutually adjacent electrodes, while the resulting voltages between each mutually adjacent pair of the then remaining electrodes was measured, and the process would be repeated until the current source had been applied between each pair of mutually adjacent electrodes and, for each pair, the corresponding voltages between each mutually adjacent pair of the remaining electrodes had been measured. All the measured data would then be processed, in known manner, by computer means (not shown) to yield a representation of the distribution of electrical resistivity in the material 20.

FIG. 1 also shows, for the case where the material 20 is of uniform electrical resistivity, the system of equipotential lines 25 and current streamlines 26 which characterize the electrical field which is produced in the material 20 by applying an input electrical signal from the source 23 between one pair of mutually adjacent electrodes 22. It will be seen that the equipotential lines 25 fan out in such a way that elements of the wall 21 at different positions round its periphery are all at different potentials, and this would remain true even if the material 20 were not of uniform resistivity and there were in consequence a greater or lesser degree of perturbation of the symmetry and regularity of the illustrated pattern of equipotential lines and current streamlines. It will be clear that the type of field pattern illustrated in FIG. I cannot obtain if the electrically insulating wall 20 is replaced by an electrically conductive wall, since, the greater its conductivity, the more closely will it approximate to an equipotential surface.

As already noted above, if the containing wall is conductive it is necessary to insulate the electrodes from it. Even if that is done, however, an input signal applied by the source 23 between two adjacent electrodes, as shown in FIG. 1, would be to a large extent short circuited by the part of the conductive wall extending between the two electrodes. An output signal measured between two other mutually adjacent ones of the electrodes would be of unacceptably low amplitude both because the field generated in the material 20 at a distance from the electrodes between which the source 23 is connected would be reduced by the short-circuiting effect of the wall between those electrodes and also because of a similar short-circuiting effect due to the presence of the conductive wall extending between the pair of electrodes between which the output signal was being measured.

In practicing the present invention, however, the input and output electrical signals are applied or measured not between pairs of electrodes but, in each case, between an individual electrode and a common electrical reference ground. In the embodiment of the invention illustrated diagrammatically in FIG. 2, in which an electrically conductive containing wall is referenced 21A to distinguish it from the insulating wall 21 of FIG. 1, this conductive containing wall serves as the common electrical reference point, or ground.

Figure 3:
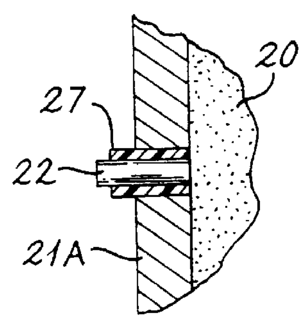
FIG. 3 is a schematic sectional view of one of a plurality of similar electrodes mounted in the electrically conductive containing wall shown in FIG. 2 but electrically insulated from the wall and from each other.

Each of the electrodes 22 mounted in the wall 21A, and numbered 1–16, respectively, is electrically insulated from the wall, for example by means of an insulating sleeve 27, as shown in FIG. 3. It may be remarked, however, that the mounting of the electrodes in the wall 21A may in practice need to be more complicated than shown in FIG. 3, since the material 20 within the wall 21A may be under substantial pressure which the electrodes and their mountings must be capable of resisting.

Figure 2:
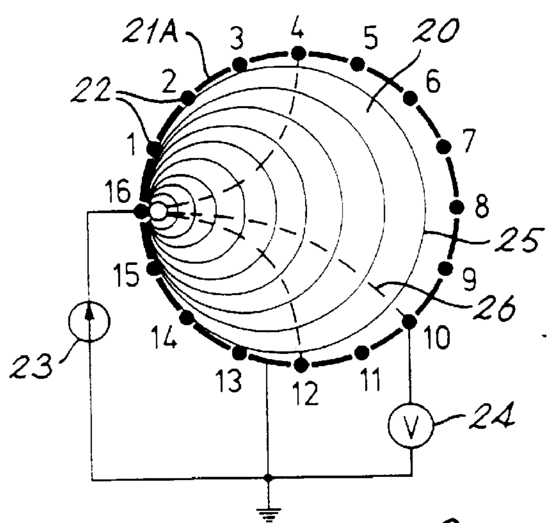
FIG. 2 represents an application of EIT in accordance with the invention to material contained in a circular-section vessel or pipeline of which the containing wall is of electrically conductive material such as a metal.
Figure 4:
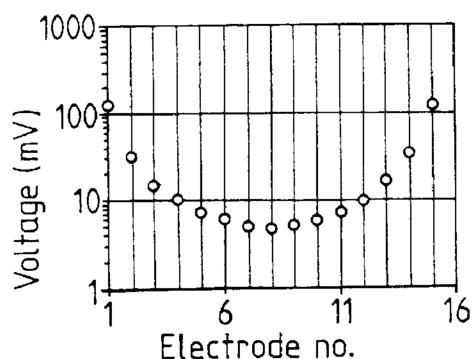
FIG. 4 represents the electrical potentials which, when a given electrical potential or current is applied to one of the electrodes shown in FIG. 2, may be measured at the other such electrodes.

In accordance with the invention, and as shown in FIG. 2, an input electrical signal provided by the source 23 is applied between ground, i.e. the conductive wall 21A, and a single one of the electrodes 22 (that numbered 16, as illustrated) while output electrical signals are measured between each of the remaining electrodes 22 (numbered 1–15 respectively) and ground, by measuring means 24 as shown connected between ground and the electrode 22 numbered 10. Corresponding sets of output signals are measured while an input signal is applied to each other of the electrodes 22 individually, and the totality of measured data is then processed by the use of an appropriate algorithm to derive a representation of the resistivity distribution within the material 20. FIG. 2 also shows, for the case of uniform resistivity of the material 20, the equipotential lines 25 and current streamlines 26 of the field pattern established in the material 20 by applying an input signal from the source 23 between ground (the wall 21 A) and the electrode 22 which is numbered 16. It will be observed that the field pattern obtained in this case is quite different from that shown in FIG. 1: in fact, the equipotential lines and current streamlines (which are always mutually orthogonal) have virtually interchanged with one another as between FIGS. 1 and 2. If, as indicated in FIG. 2, the input signal is an injected current (for example of 1.5 mA per cm peak-to-peak at a frequency of 9.6 kHz) applied to one electrode 22 and the output signals are the potentials of the other electrodes 22 relative to the wall 21A (from which, of course, they are insulated) those electrodes which are remote from that one to which the input signal is applied from the source 23 are relatively unaffected by the input signal, while the effect is progressively greater on those electrodes which are closer. This is illustrated by FIG. 4, which shows typical voltages measured (in millivolts) at each of the electrodes numbered 1-15 when the input signal is applied to the electrode numbered 16, as shown in FIG. 2. The voltage output signals thus obtained are substantially greater than would be measured between pairs of adjacent electrodes, with the same input signal applied between one such pair (as described with reference to FIG. 1) but subject to the grounding or short-circuiting effect which is produced by an electrically conductive wall even though the electrodes are insulated from it.

The presence of the insulators 27, and the corresponding absence there of conductive material continuous with that of the wall 21A and at ground potential, has a slight distorting effect on the field pattern in the material 20 immediately adjacent the electrodes. It may be shown that this effect results in the potential measured at an electrode being similar to that which would be measured by an electrode positioned a distance s/4 inside the wall if the wall presented a continuous surface at ground potential, where s is the external diameter of the insulator 27. That is, if the actual radius of the wall 21A is $R_o$, the radius of the circle on which the electrodes are disposed is effectively $R_e$ where $R_e=R_o-s/4$. An "intrusive effect", g, of the presence of the insulators of diameter s can then be defined as $g = R_{o/Re}$. Since $s<<R_o$, the distortion of the electric field produced in the material 20 by applying a current to one of the electrodes 22 is greatest in the vicinity of the wall 21A but rapidly becomes negligible at smaller radii.

It may be shown that, for a material 20 of uniform conductivity σ, injection at one electrode 22 of a current IL produces, at an electrode spaced round the wall 21A by an angle (π−θ), a voltage $V(R_e,\theta)$ given by $$V(R_e,\theta)=\frac{I_L}{4\pi\sigma}\log_e\left[\frac{\lambda^4+2\lambda^2\cos\theta+1}{2\lambda^2(1+\cos\theta)}\right].\ (\theta\neq\pi)$$

This is the distribution of induced voltage on the electrodes which is illustrated in FIG. 4. The similarity between this voltage profile and that obtained in the case of an insulating vessel wall, by applying an input current signal between a pair of adjacent electrodes as described above with reference to FIG. 1, provided an early confirmation that the present invention may be practiced using data acquisition systems (source 23 and output signal measuring means 24) already available for use with a non-conductive vessel wall, with at most only minor modifications to the current injection and voltage buffer circuitry being required.

Figure 5:
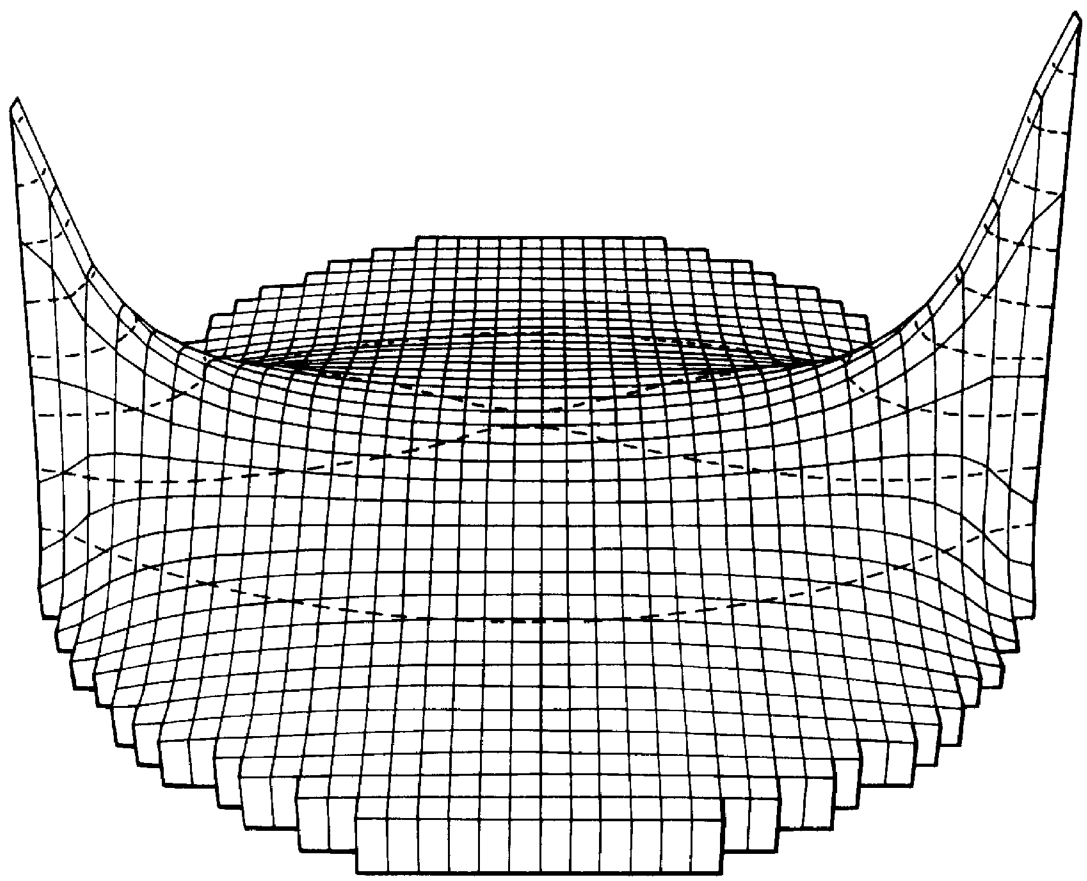
FIG. 5 is a representation of pixel sensitivity coefficients as used in implementing an image reconstruction in accordance with the invention.

In the case of non-uniformity of the conductivity of the material 20, essentially the same image reconstruction algorithms may be employed when the container wall is of electrically conductive material as are already known and in use in connection with EIT of material contained within a non-conductive pipeline or other vessel. For example, in practicing the invention in conjunction with an electrically conductive container wall, as described above with reference to FIG. 2, use has been made of a qualitative image reconstruction algorithm employing the sensitivity coefficient method described by C. J. Kotre in Clin. Phys. Physiol. Meas., 1989, 10(3), 275–281. FIG. 5 shows the sensitivity coefficients of the pixels for the case where the electrodes to which an input signal is applied and at which an output signal is measured are diametrically opposite to one another, as for example the electrodes numbered 16 and 8 in FIG. 3.

Figure 6:
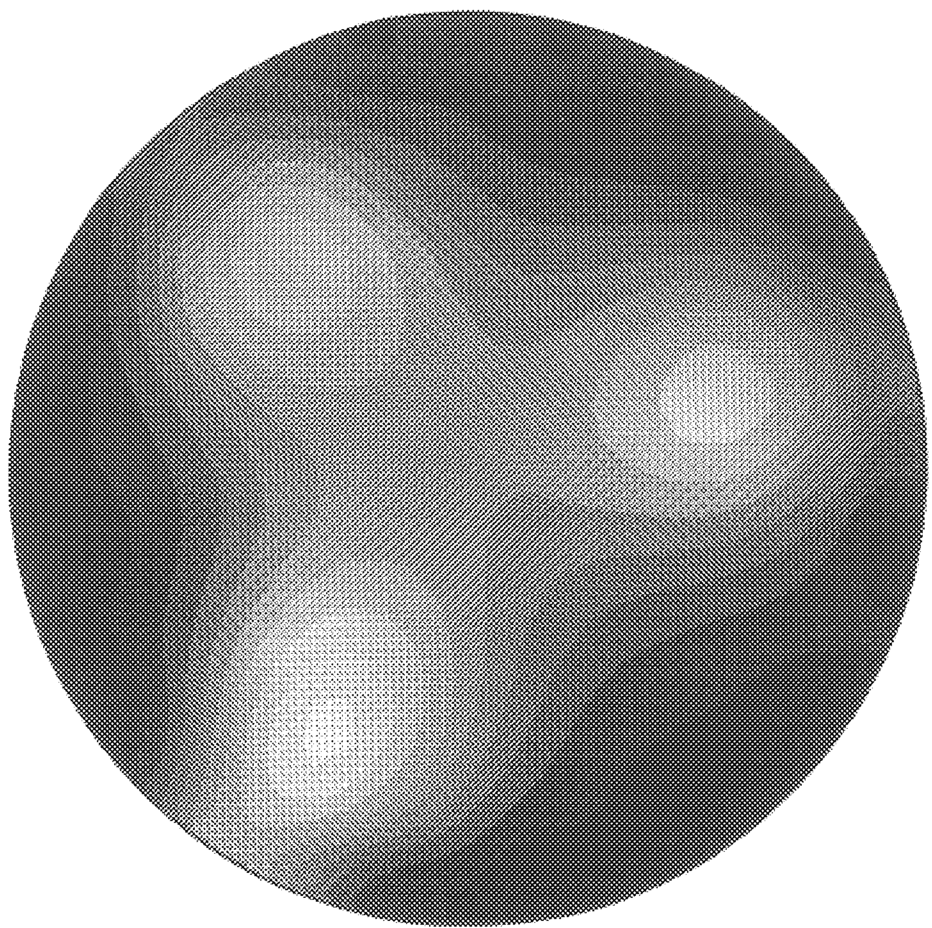
FIG. 6 is a reconstructed image of three glass rods dipping into water contained in a metal-walled vessel.

It can be seen that there is a high sensitivity in the regions close to both electrodes but that the sensitivity decreases rapidly away from those regions. By utilizing a sequence of sensitivity maps, corresponding to all the possible drive/ measure combinations, a qualitative image is reconstructed showing the variations in conductivity across the cross-section of the material 20 within the vessel 21A at the level of the electrodes 22. FIG. 6 shows a reconstructed image, obtained in this way, of three 1-cm diameter glass rods spaced approximately 2 cm from the boundary of the vessel 21A of 16.6 cm diameter which was filled with tap water. The regions of lighter shade in FIG. 6 represent areas of relatively low conductivity and correspond to the positions of the three glass rods, and the darker parts of the image correspond to the surrounding water.

The sensitivity theorem for an electrically conducting body, as originally developed by Geselowitz and later refined by Lehr, in essence enabled the impedance properties of a body to be determined from a 4-electrode (two-port) current excitation/ voltage measurement technique as illustrated in FIG. 1. However, the theorem was developed on the basis that the outer layer of the body was electrically non-conducting. For the purpose of the present invention, the original four-lead two-port model is modified into an equivalent three-lead two-port model with, in the example shown in FIG. 2, the conducting boundary wall 21A serving as the third lead. Despite this modification, the Geselowitz/ Lehr theorem is unchanged and the discretized area representing a two-dimensional cross-section of the vessel can be treated with Geselowitz's method to determine the sensitivity coefficient of each of the discretized regions. In the image shown in FIG. 6 the circular cross-section of the vessel was divided into a set of 7,680 square pixels having a radius of 100 square pixels. The sensitivity coefficient S for each of these pixels was calculated using the Geselowitz method, and the reconstructed image composed of pixel grey-levels $P_{x,y}$ was formed, as proposed by Kotre, from the product of these coefficients with the logarithm of the ratio of measured voltages.

It will be understood that although the image shown in FIG. 6 was obtained by use of an image reconstruction algorithm employing the Kotre sensitivity coefficient method, other known methods of processing the measured data to obtain the desired image may also be employed. For example, a finite element method (FEM), appropriately matched to the changed boundary conditions, may equally well be employed.

It will be understood that although the foregoing specification refers to resistance and resistivity of the material under investigation, EIT generally and the present invention in particular may be used for investigating impedance generally and not only its resistive component; and that accordingly the references to resistance and resistivity are to be understood in the wider sense of impedance.

It will be understood also that, although the invention is particularly adapted for use in overcoming the difficulties encountered in applying EIT in conjunction with a container wall of electrically conductive material, it may with advantage also be applied in the case of vessels having electrically non-conductive walls or, indeed, in clinical use where the boundary of the sample is the patient's skin which is of high impedance in directions along the surface. In such cases, of course, it is not possible to use the (non-conductive) container wall as the common electrical reference ground, but other arrangements may be made, for example as will now be described with reference to FIGS. 7 and 8.

Figure 7:
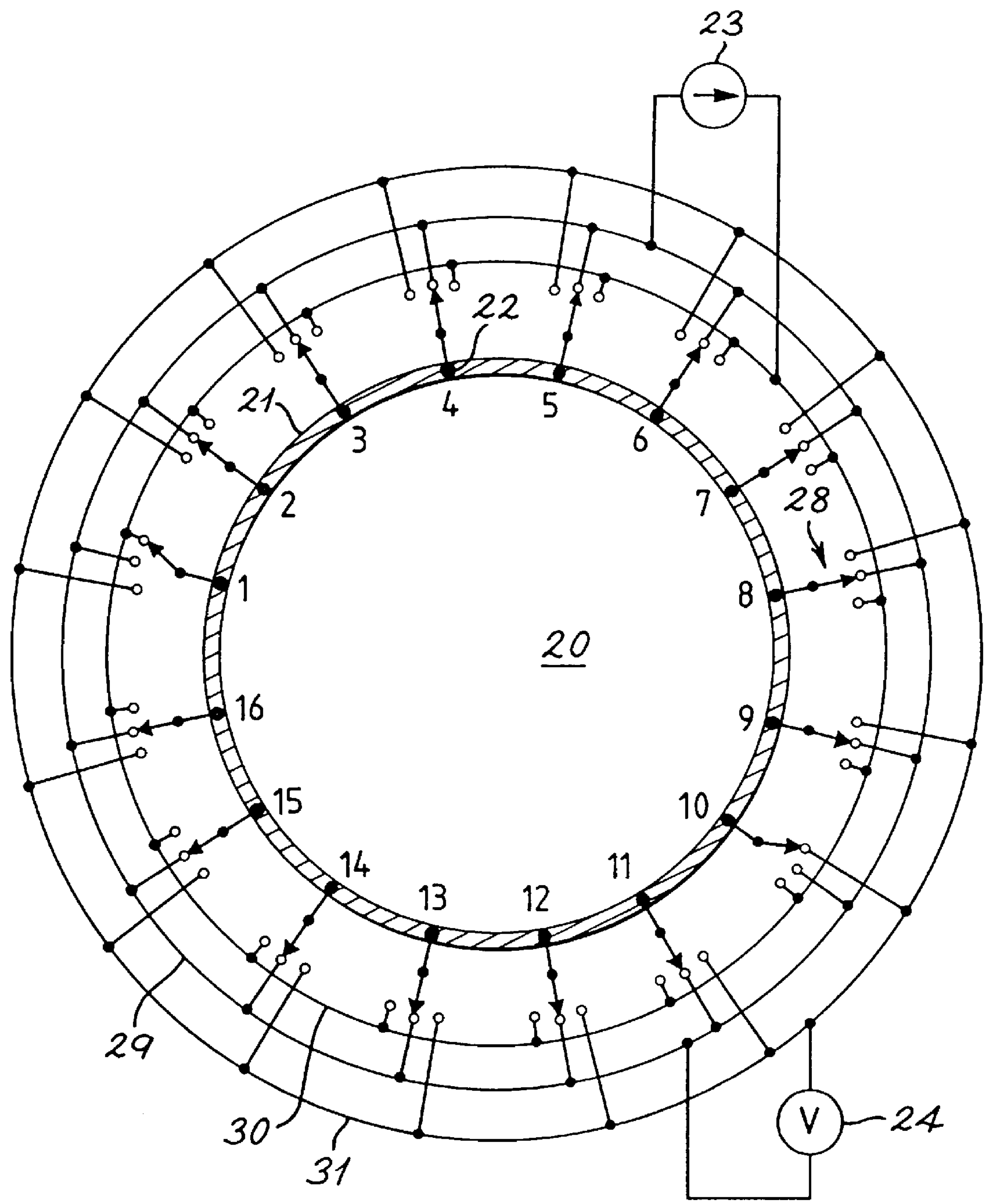
FIG. 7 represents an electrically non-conductive vessel wall fitted with a plurality of electrodes and illustrates a suitable arrangement of electrode connections for use in carrying out the invention.

As shown in FIG. 7, material 20, of whose impedance distribution an image is to be reconstructed, is contained within a pipeline or other vessel having an electrically non-conductive wall 21 in which are mounted, protruding through the wall into electrical contact with the material 20, a plurality of electrodes 22 numbered I to 16. Also provided are a source 23 for applying input electrical signals to selected electrodes 22 and an output signal measuring device 24 for measuring output signals from selected electrodes 22. Thus far, the arrangement is as described with reference to FIG. 1 of the aforementioned co-pending application. As shown in FIG. 7, however, each electrode 22 is connected to a respective 3-way switch 28 by which it can be connected to a common connector strap 29 to serve as part of a reference ground of the system, or to a connection 30 or to a connection 31. The signal source 23 is connected to apply input signals between the reference ground strap 29 and the connection 30 and any electrode 22 connected thereto, and the signal measuring means 24 is similarly connected to measure output signals generated between the strap 29 and the connection 31 and any electrode connected thereto. In use of this system, at any given moment during data collection all the electrodes 22 are connected by their respective switches 28 to the strap 29 to form a reference ground of the system, except for one electrode 22 (that numbered I as shown in FIG. 7) which is switched to receive an input signal applied by the source 23 between it and the reference ground, and one (that numbered 10 as shown in FIG. 7) which is connected to the connection 31 to provide an output signal to the device 24. Each of the electrodes 22 is connected, separately, to the connection 29 for application to it of an input signal during an interval during which each other electrode, separately, is connected to the connection 31 for measurement of an output signal by the device 24. Thus at any time all except two of the electrodes combine to provide the system reference ground.

Figure 8:
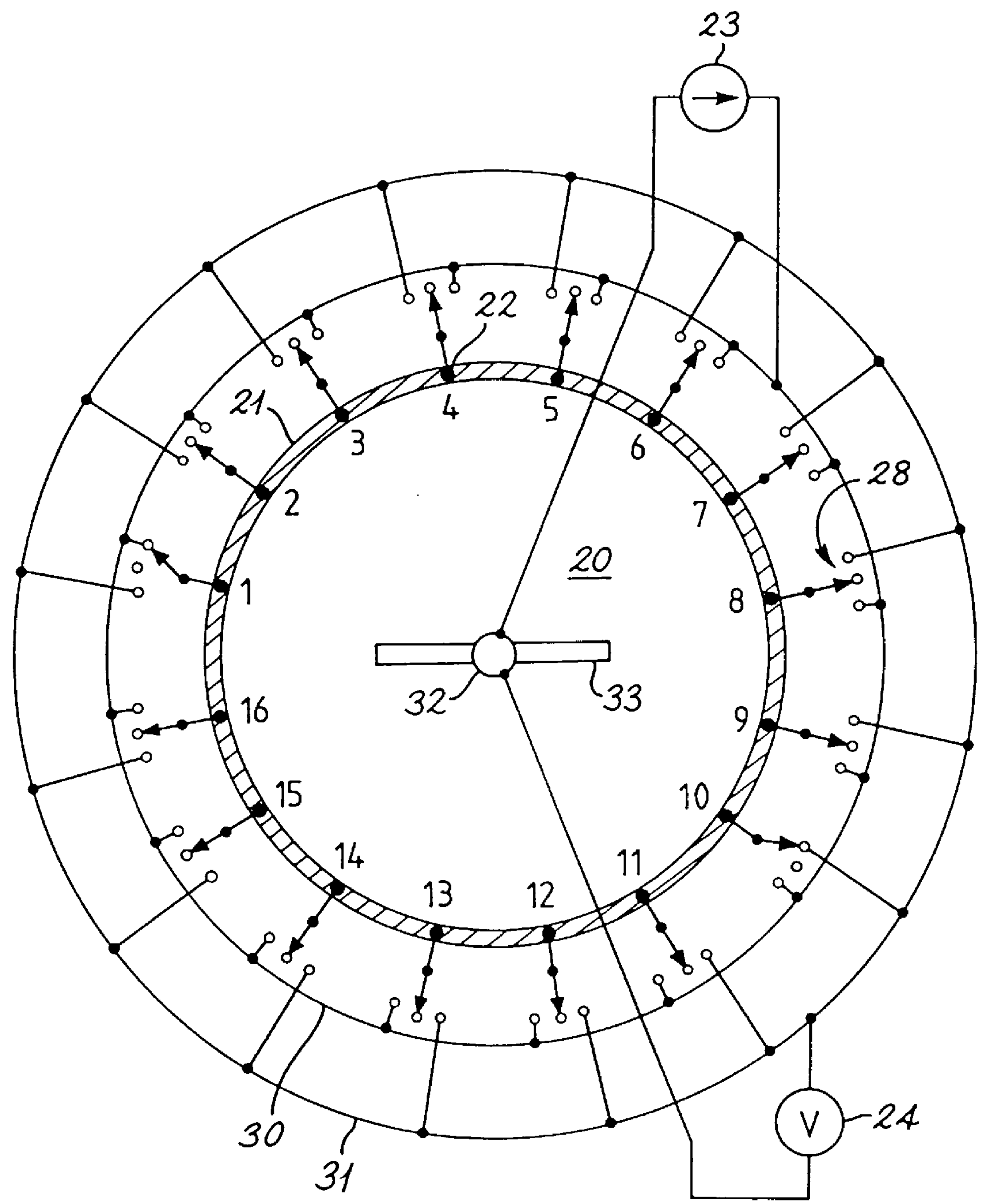
FIG. 8, similar to FIG. 7, illustrates another suitable arrangement of electrode connections for use in carrying out the invention.

The arrangement shown in FIG. 8 is generally similar to that described above with reference to FIG. 7, but is provided, within the vessel containing the material 20, with a stirrer having an electrically conductive shaft 32 with paddle blades 33 which may be non-conductive. In this case the stirrer shaft 32 serves as the reference ground and the signal source 23 and measuring device 24 are connected between the stirrer and, respectively, the connections 30 and 31. The strap 29 shown in FIG. 7 may be omitted as shown, and any electrode 22 which is not connected by its switch 28 to the connection 30 or 31 is then left disconnected and floating. It will be understood that the algorithms used in processing the measured data obtained as described with reference to FIGS. 7 and 8, or in further variants described below, will usually require appropriate, modification to take account of the particular boundary conditions set up by the electrode connections. Use of a reference ground electrode at or near the centre of the vessel as shown in FIG. 8 is effective to increase the sensitivity of the system near the centre of the vessel where, otherwise, it is low compared with the sensitivity near the peripheral boundary.

If a stirrer or other electrode as shown in FIG. 8 is provided within the material 20 in an arrangement which is otherwise as shown in FIG. 7, it may also be provided, like each peripheral electrode 22, with switch means to connect it either to the reference ground connection 29 or via the connections 30 and 31 to either the input signal source 23 or the output signal measuring means 24. This enables an input signal to be applied to it while an output signal is measured at each of the electrodes 22, one after another, and also enables successive output signals to be measured at the inner electrode as input signals are applied to each of the electrodes 22, one after another. By this means additional measurement data can be acquired which improves the sensitivity of the system in respect of parts of the material 20 which are remote from the wall 21.

It may be mentioned here that, analogous with FIG. 8, or with the above-described modification of FIG. 7 to provide it with an inner electrode at which an input signal may be applied or an output signal may be measured, or which may serve as the, or part of the, signal reference ground, such an inner electrode may similarly be employed when single-electrode excitation and measurement in accordance with the invention are employed in clinical practice. Thus in EIT thoracic examinations in accordance with the invention, an inner electrode at the free end of an insulated cable may be passed down the oesophagus to the required level within the thorax (as has indeed already been proposed in the case of conventional EIT using two-electrode signal input and two-electrode output signal measurement).

As illustrated by FIGS. I and 2, the provision of an electrically conductive boundary round the body of material which is to be investigated has the effect of interchanging the pattern of equipotential lines and current streamlines in the body, as compared with the case where the boundary is non-conductive. There may be circumstances in which advantage can be taken of this fact in the clinical use of EIT. For example, the electrodes to be applied to a patient may be mounted in insulated manner in a band or belt of electrically conductive (and preferably elastic) material which can then be fitted round the part of the patient which is to be investigated. Or the belt may be of non-conductive material, but fitted with compound electrodes such as those suggested in a paper: "Using Compound Electrodes in EIT" (Ping Hua et al, IEEE Trans. in Biomed. Eng., 40, No. 1 (Jan 1993)). As there proposed, a compound electrode comprises a small inner electrode surrounded by an outer electrode of much larger surface area, the intention being that an input current signal can be applied between the outer electrodes of two compound electrodes while an output voltage signal is measured between the inner electrodes of the same or a different pair of compound electrodes. A belt of such compound electrodes may also, however, be used in carrying out EIT in accordance with the present invention if it is fitted to a patient and all its outer electrodes are strapped together as an effective conductive outer boundary and as a signal reference ground, while input and output signals, relative to the reference ground, are applied to or measured at individual inner electrodes of the compound electrodes.

We claim:

1. A method of obtaining a representation of the distribution of electrical impedance within material contained within a containing wall, the method comprising:

providing a plurality of mutually spaced electrodes mounted at spaced locations of the wall, the electrodes being electrically insulated from one another and arranged to be in electrical contact with material contained within the wall;

applying, between an electrical reference ground and each electrode, sequentially, an input electrical signal which, while applied to any one of the electrodes, causes respective output electrical signals to be generated between the electrical reference ground and each other one of the electrodes;

measuring said output electrical signals generated between the electrical reference ground and each other one of the electrodes; and processing the resulting measured data to provide a representation of the distribution, within said material, of its electrical impedance.

2. A method as claimed in claim 1 wherein the containing wall is electrically conductive and is employed as said electrical reference ground relative to which the input and output electrical signals are applied and measured.

3. A method as claimed in claim 1 wherein the containing wall is electrically non-conductive, and wherein said electrical reference ground is formed by connecting together, at any one time, all the electrodes except those two electrodes at which, respectively, an input signal is being applied and an output signal is being measured.

4. A method as claimed in claim 1 further comprising providing, as said electrical reference ground, an electrode within, and spaced from the boundary of, said material.

5. A method as claimed in claim 1, in clinical uses wherein said containing wall comprises the skin of a patient and wherein the electrodes are applied in contact with the skin.

6. A method as claimed in claim 5, wherein the electrodes are fitted to a belt and the belt is fitted around a part of the patient.

7. A method as claimed in claim 6, wherein the belt is electrically conductive and electrically insulated from the electrode and is employed as said electrical reference ground.

8. Apparatus for obtaining a representation of the distribution of electrical impedance within a body of material, the apparatus comprising:

a container having a containing wall for containing the material;

a plurality of electrodes mounted at spaced locations of the wall, electrically insulated from one another and arranged to be in electrical contact with material contained within the wall;

means for generating, and for applying between an electrical reference ground and each electrode, sequentially, an input signal which, while applied to any one of the electrodes, causes respective output electrical signals to be generated between the electrical reference ground and each other one of the electrodes;

means for measuring the output electrical signals generated between the electrical reference ground and each other one of the electrodes; and means for processing the resulting measured data and providing a representation of the distribution, within said material, of its electrical impedance.

9. Apparatus as claimed in claim 8, wherein said electrodes are mounted in the wall and protrude therethrough to be in electrical contact with the material contained within the wall.

10. Apparatus as claimed in claim 9, wherein said containing wall is electrically conductive and the electrodes mounted in it are electrically insulated from it.

11. Apparatus as claimed in claim 8, wherein the containing wall is electrically conductive and constitutes said electrical reference ground relative to which the input and output electrical signals are applied and measured.

12. Apparatus as claimed in claim 8 wherein the containing wall is electrically nonconductive and, for constituting said electrical reference ground, there are provided switch means for connecting together, at any one time, all the electrodes except those two electrodes at which, respectively, an input signal is being applied and an output signal is being measured.

13. Apparatus as claimed in claim 8, and including, as the electrical reference ground, an electrode within, and spaced from the boundary of, said material.

14. Apparatus as claimed in claim 13, wherein the electrical reference ground is constituted by means, such as a stirrer, which also serves another purpose.

15. Apparatus as claimed in claim 8, in clinical use, wherein the electrodes are arranged for contact with a patient's skin.

16. Apparatus as claimed in claim 15, wherein the electrodes are fitted to a belt and the belt is fitted around a part of the patient.

17. Apparatus as claimed in claim 16, wherein the belt is electrically conductive and electrically insulated from the electrodes and constitutes said electrical reference ground.

* * * * *